(12) United States Patent
Ackerman

(10) Patent No.: US 9,986,867 B2
(45) Date of Patent: Jun. 5, 2018

(54) NASAL RINSE SYSTEM

(71) Applicant: Gary Wayne Ackerman, Sterling, VA (US)

(72) Inventor: Gary Wayne Ackerman, Sterling, VA (US)

(*) Notice: Subject to any disclaimer, the term of this patent is extended or adjusted under 35 U.S.C. 154(b) by 578 days.

(21) Appl. No.: 14/493,447

(22) Filed: Sep. 23, 2014

(65) Prior Publication Data

US 2016/0081511 A1 Mar. 24, 2016

(51) Int. Cl.
*A47J 27/21* (2006.01)
*A47J 27/212* (2006.01)
*A61M 3/02* (2006.01)
*A61J 1/22* (2006.01)

(52) U.S. Cl.
CPC ......... *A47J 27/2105* (2013.01); *A47J 27/212* (2013.01); *A47J 27/21041* (2013.01); *A61J 1/22* (2013.01); *A61J 2200/42* (2013.01); *A61M 3/0245* (2013.01); *A61M 2210/0618* (2013.01)

(58) Field of Classification Search
None
See application file for complete search history.

(56) References Cited

U.S. PATENT DOCUMENTS

| | | | | |
|---|---|---|---|---|
| 2,660,658 A * | 11/1953 | Wagner | ............ | A47J 27/62 219/433 |
| 3,129,318 A * | 4/1964 | Morrison | ............ | A47J 31/053 215/12.1 |
| 3,896,973 A * | 7/1975 | Morgan | ............ | A45D 34/00 219/433 |
| 3,969,610 A * | 7/1976 | Ratti | ............ | A47J 27/62 219/435 |
| 4,399,351 A * | 8/1983 | Koff | ............ | A47J 27/004 219/430 |
| 4,463,249 A * | 7/1984 | Narita | ............ | G05B 9/02 219/432 |
| 6,316,750 B1 * | 11/2001 | Levin | ............ | A61F 7/0241 219/386 |
| 6,555,792 B1 * | 4/2003 | Elsener | ............ | B01J 19/0093 219/385 |
| 6,953,914 B2 * | 10/2005 | Suzuki | ............ | A47J 36/2433 165/64 |
| 7,854,387 B2 * | 12/2010 | Kammer | ............ | A61M 5/445 219/430 |

(Continued)

*Primary Examiner* — Joseph M Pelham
(74) *Attorney, Agent, or Firm* — Dunlap Bennett & Ludwig PLLC

(57) ABSTRACT

A method of controllably heating nasal rinsing solution inside a neti pot is provided. The method comprises the following steps: providing a nasal rinse system comprising: a neti pot having a main body forming a cavity for receiving a rinsing solution; a spout extending from a top portion of the main body; an opening defined by a top portion of the main body, wherein the opening communicates with the cavity; a lower portion of the main body incorporating a heating element electrically connected to a power source, wherein the heating element provides a thermostat for determining the heat at the heating element; and at least one indicator light that is electrically connected to the thermostat so that the at least one indicator light is activated when the said heat reaches a predetermined temperature; pouring the rinsing solution through the opening; and waiting for the at least one indicator light to by activated.

9 Claims, 3 Drawing Sheets

(56) References Cited

U.S. PATENT DOCUMENTS

| | | | |
|---|---|---|---|
| 8,309,891 B2* | 11/2012 | Kammer | A61M 3/0245 |
| | | | 219/432 |
| 8,789,534 B2* | 7/2014 | Faries, Jr. | A61B 46/10 |
| | | | 128/849 |
| 2008/0294124 A1* | 11/2008 | Mehta | A61M 3/0245 |
| | | | 604/260 |
| 2011/0139824 A1* | 6/2011 | Cacka | A61M 3/0245 |
| | | | 604/275 |
| 2013/0041329 A1* | 2/2013 | Huy | A61M 3/0241 |
| | | | 604/257 |
| 2015/0018760 A1* | 1/2015 | Hardin | A61M 3/0266 |
| | | | 604/82 |
| 2015/0209457 A1* | 7/2015 | Bonutti | A61L 2/10 |
| | | | 250/435 |

* cited by examiner

NASAL RINSE SYSTEM

BACKGROUND OF THE INVENTION

The present invention relates to nasal rinse devices and, more particularly, to a nasal rinse system combining a nasal rinse device and a heating element.

The benefits of rinsing one's sinus cavities have been well established, and vessels for nasal cavity rinsing are well known in the prior art. However, the use of warm tap water in such vessels is dangerous due to possible contaminants, and so use of distilled water or the like is a must. Which in turn means such distilled water needs to be heated. However, such vessels have no built in means for heating the distilled water, and so must employ disparate heating elements such as saucepans, tea pots, microwavable cups and the like, which are inconvenient, possibly unsafe if not designed to fill such vessels, and cannot properly control the temperature of the heated distilled water.

As can be seen, there is a need for a vessel for nasal cavity rinsing that incorporates a heating element to controllably heat the distilled water to temperatures comfortable for sinus rinsing.

SUMMARY OF THE INVENTION

In one aspect of the present invention, a system for controllably heating nasal rinsing solution inside a neti pot, comprises: a neti pot comprising: a main body forming a cavity for receiving a rinsing solution; a spout extending from a top portion of the main body; an opening defined by a top portion of the main body, wherein the opening communicates with the cavity; and a lower portion of the main body forming an alignment recess, wherein the alignment recess provides a thermostat; a heating unit comprising: a heating element electrically connected to a power source, wherein the heating element provides an outward surface for generating heat; an alignment nub formed by the outward surface, wherein the alignment nub cooperates with the alignment recess to removably mate thereto; and at least one indicator light that is electrically connected to the thermostat when the alignment recess and the alignment nub are mated.

In another aspect of the present invention, method of controllably heating nasal rinsing solution inside a neti pot, comprises the steps of: providing a neti pot comprising: a main body forming a cavity for receiving a rinsing solution; a spout extending from a top portion of the main body; an opening defined by a top portion of the main body, wherein the opening communicates with the cavity; and a lower portion of the main body forming an alignment recess; providing a heating unit comprising: a heating element electrically connected to a power source, wherein the heating element provides an outward surface for generating heat and provides a thermostat for determining said heat; an alignment nub formed by the outward surface, wherein the alignment nub cooperates with the alignment recess to removably mate thereto; and at least one indicator light that is electrically connected to the thermostat so that the at least one indicator light is activated when the said heat reaches a predetermined temperature; mating the alignment recess and the alignment nub; pouring the rinsing solution through the opening; and waiting for the at least one indicator light to by activated.

In yet another aspect of the present invention, method of controllably heating nasal rinsing solution inside a neti pot, comprises the steps of: providing a neti pot comprising: a main body forming a cavity for receiving a rinsing solution; a spout extending from a top portion of the main body; an opening defined by a top portion of the main body, wherein the opening communicates with the cavity; a lower portion of the main body incorporating a heating element electrically connected to a power source, wherein the heating element provides a thermostat for determining the heat at the heating element; and at least one indicator light that is electrically connected to the thermostat so that the at least one indicator light is activated when the said heat reaches a predetermined temperature; pouring the rinsing solution through the opening; and waiting for the at least one indicator light to by activated.

These and other features, aspects and advantages of the present invention will become better understood with reference to the following drawings, description and claims.

DETAILED DESCRIPTION OF THE INVENTION

The following detailed description is of the best currently contemplated modes of carrying out exemplary embodiments of the invention. The description is not to be taken in a limiting sense, but is made merely for the purpose of illustrating the general principles of the invention, since the scope of the invention is best defined by the appended claims.

Broadly, an embodiment of the present invention provides a method of controllably heating nasal rinsing solution inside a neti pot, comprising the steps of: providing a nasal rinse system comprising: a neti pot having a main body forming a cavity for receiving a rinsing solution; a spout extending from a top portion of the main body; an opening defined by a top portion of the main body, wherein the opening communicates with the cavity; a lower portion of the main body incorporating a heating element electrically connected to a power source, wherein the heating element provides a thermostat for determining the heat at the heating element; and at least one indicator light that is electrically connected to the thermostat so that the at least one indicator light is activated when the said heat reaches a predetermined temperature; pouring the rinsing solution through the opening; and waiting for the at least one indicator light to by activated.

Figure 1:
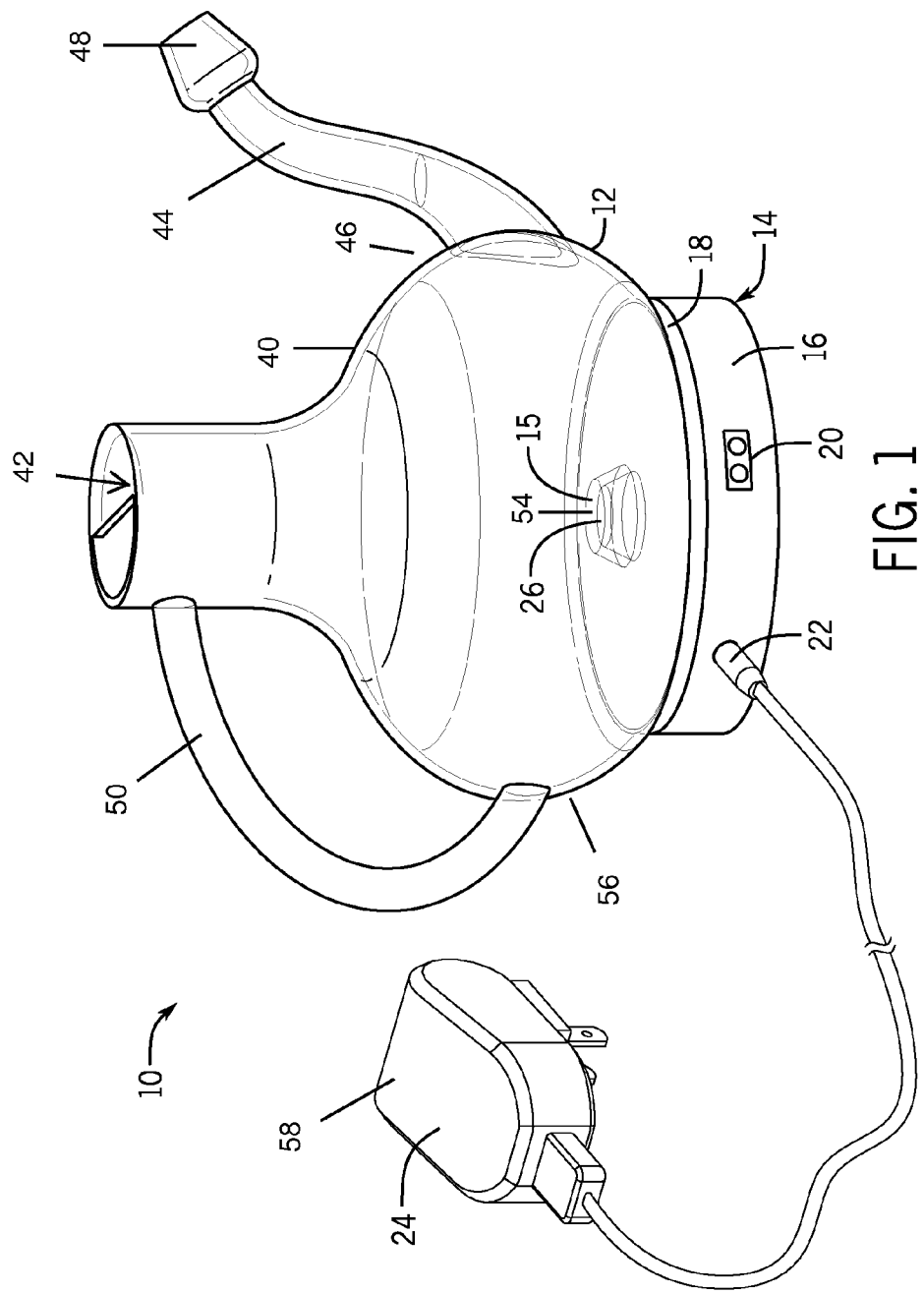
FIG. 1 is a front perspective view of an exemplary embodiment of the present invention.
Figure 2:
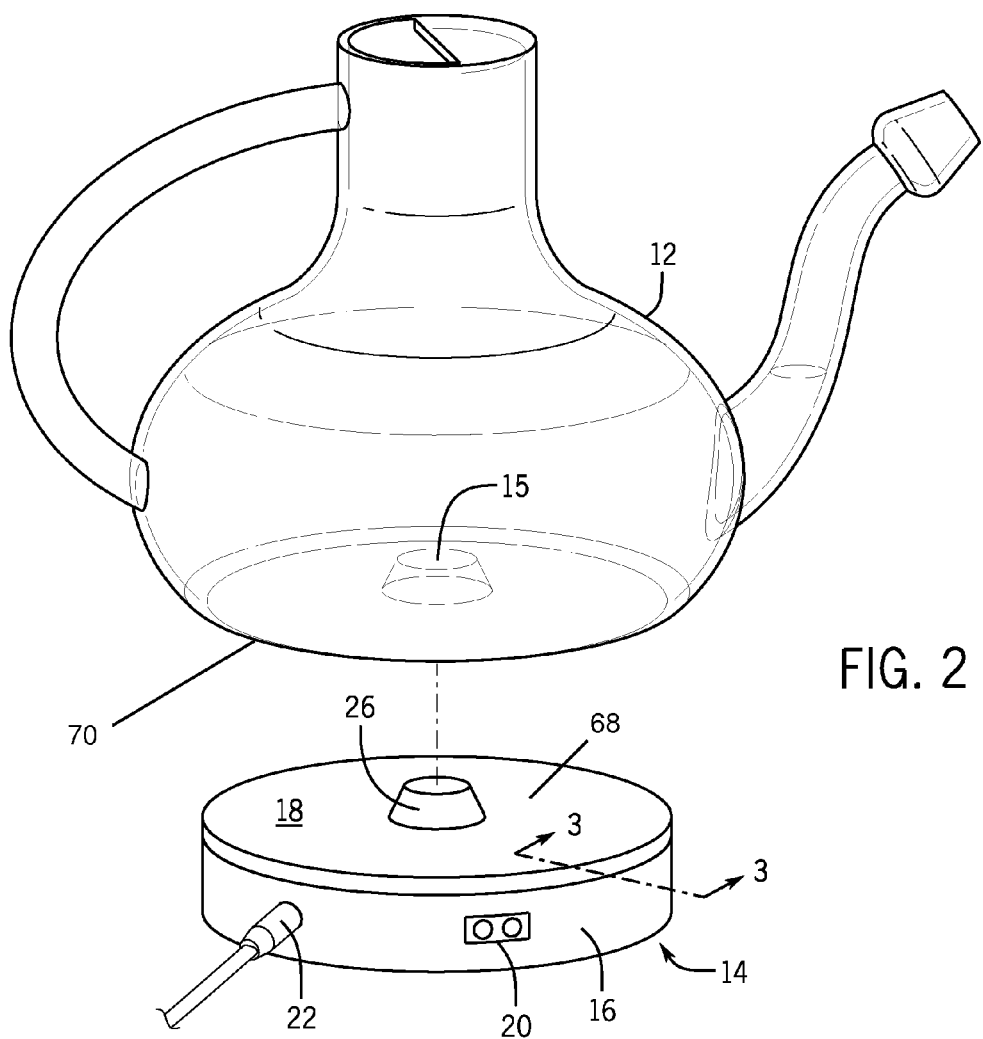
FIG. 2 is an exploded perspective view of an exemplary embodiment of the present invention.
Figure 4:
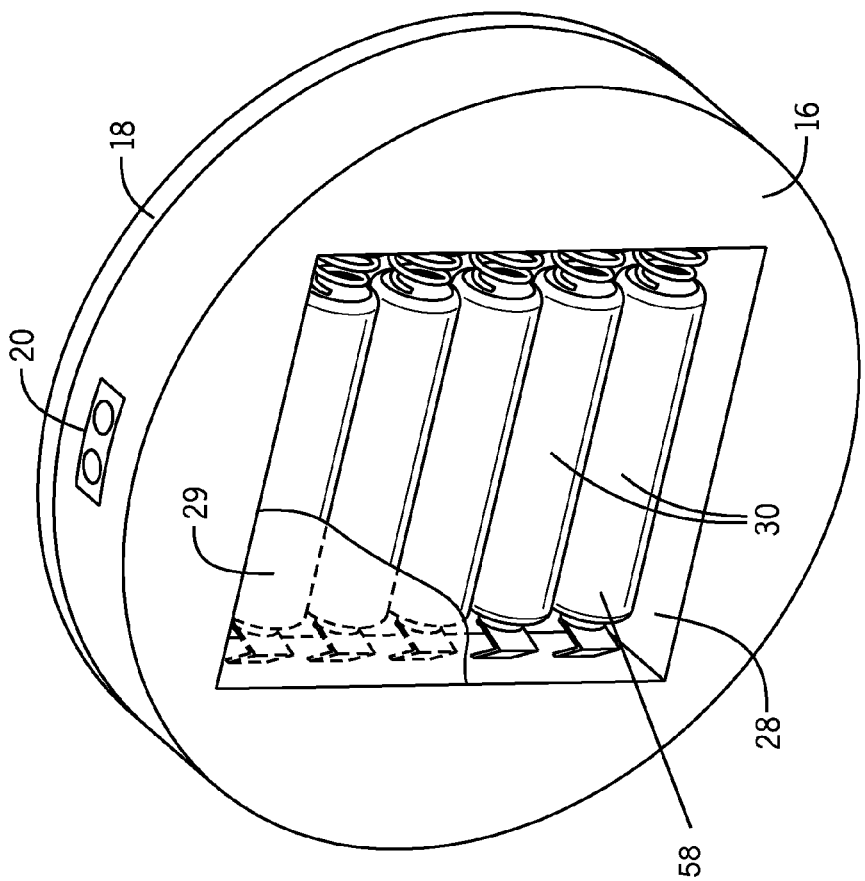
FIG. 4 is a bottom perspective view of an exemplary embodiment of the present invention, with parts broken away.
Figure 3:
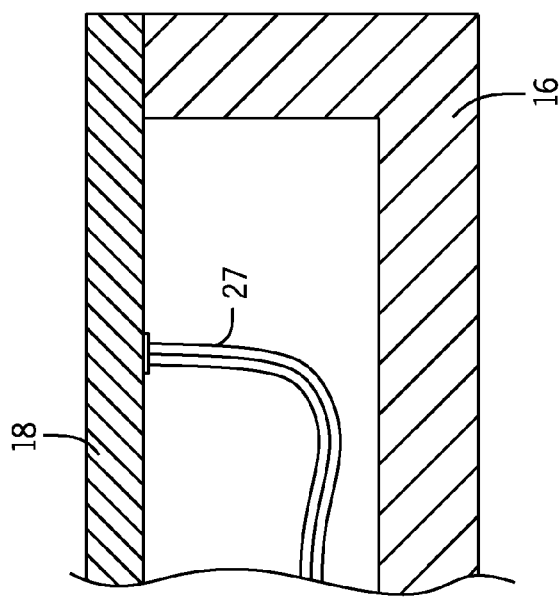
FIG. 3 is a cross-sectional view of an exemplary embodiment of the present invention, taken along line 3-3 of FIG. 2.

Referring to FIGS. 1 through 4, a nasal rinse system 10 embodies an system and a method of the present invention for use in rinsing a user's nasal passages. The nasal rinse system 10 may include a neti pot 12, a complementary heater unit 14 and a power source 58.

The neti pot 12 may include a main body 40 defining a cavity 42 for receiving a fluid, such as a sinus rinsing solution. The neti pot 12 may be made of thermal conductive material such as ceramic, metal or the like. A spout 44 is formed and extends off a front portion 46 of the main body 40 of the neti pot 12. The spout 44 may include a nozzle 48 having an opening through which the fluid inside the cavity 42 of the neti pot 12 may pass when the neti pot 12 is tipped to allow the fluid to flow into the spout 44 and out of the nozzle opening. The neti pot 12 may include a handle 50 extending from the opposite or back portion 56 of the neti pot 12 so that a user can easily lift and control the orientation of the neti pot 12. A top portion 60 of the main body 40 defines an opening through which the cavity 42 of the neti pot 12 is filled with the fluid. A lower portion 70 of the main body 40 may provide a thermostat 54. The thermostat 54 may include a thermal sensor or the like for determining the temperature of the lower portion 70 of the main body 40 and/or the fluid positioned within its cavity 42.

In certain embodiments, an alignment recess 15 may be formed in the lower portion 70 of the main body 40 of the neti pot 12 and is configured to be positioned over and mated with an alignment nub 26 of the heater unit 14 in order to provide a secure removable mounting between the heater unit 14 and the main body 40. In certain embodiments, the thermostat 54 may be provided by and electrically connected to the alignment recess 15 for facilitating the determination of the fluid positioned within the cavity 42. The alignment nub 26 may close an open circuit when mated within the alignment recess 15 so as to electrically interconnect the power source 58 and the thermostat 54. In an alternative embodiment, said closure of the open circuit may electrically connect a heating element 18.

The heater unit 14 may include a unit body 16 and a heating element 18. The unit body 16 provides at least one indicator light 20. The thermostat 54 may be electrically connected to the power source 58 and the at least one indicator light 20 so that the when the fluid positioned in a portion of the cavity 42 reaches a predetermined temperature range then the at least one indicator light 20 is electrically activated to emit a light. The predetermined temperature range may be between 96 and 99 degrees Fahrenheit. In certain embodiments, the power source 54 is electrically disconnected when the predetermined temperature range has been achieved. In an alternative embodiment, the heater unit 14 may not have the raised alignment nub 26, and so have a generally flat heating element 18.

The heater element 18 may provide an outward surface 68. The outward surface 68 may form the alignment nub 26 disposed to near the center of the outward surface 68. The heater element 18 may be electrically connected to the power source 58 so as to generate heat along at least a portion of the outward surface 68. The power source 58 may include a power cord having a plug 22 and electrical connections 27 adapted to electrically connect to an external power supply 24. In an alternative embodiment, the power source 58 includes a battery 30 disposed within a compartment 28 formed with the unit body 16. A closure 29 may be removably engaged to the unit body 16 of the heater unit 14 so as to enclose the compartment 28. The heating unit 14 may include a control element for controlling the heat generated by the heating element 18.

In an alternative embodiment, the heater unit 14 may be integrated into the lower portion 70 of the main body 40 of the neti pot 12.

A method of using the present invention may include the following. The nasal rinse system 10 disclosed above may be provided. The cavity 42 may be filled with a rinsing solution through a user pouring said rinsing solution through the opening of the top portion 60 of the main body 40. Then the user may mate the alignment recess 15 with the alignment nub 26 on the heating unit 14 so as to electrically connect the thermostat 54, the power source 58, the heating element 18 and the at least indicator light 20, whereby the heating element 18 generates heat to at least a portion of the outward surface 68 of the heating element 18. When the thermostat 54 provided by the alignment recess 15 determines the temperature of at least a portion of the rinsing solution positioned within the cavity 42 to be within the predetermined temperature range, then the at least one indicator light 20 may be activated to indicate to the user to satisfactory condition of the rinsing solution within the neti pot 12.

In certain embodiments, the heating element 18 and/or power source 58 may be integrated with the lower portion 70 of the neti pot 12.

It should be understood, of course, that the foregoing relates to exemplary embodiments of the invention and that modifications may be made without departing from the spirit and scope of the invention as set forth in the following claims.

What is claimed is:

1. A system for controllably heating nasal rinsing solution inside a neti pot, comprising:
   a neti pot comprising: a main body forming a cavity for receiving a rinsing solution; a spout extending from a top portion of the main body; an opening defined by a top portion of the main body, wherein the opening communicates with the cavity; and a lower portion of the main body forming an alignment recess, wherein the alignment recess provides a thermostat; and
   a heating unit comprising: a heating element electrically connected to a power source, wherein the heating element provides an outward surface for generating heat; an alignment nub formed by the outward surface, wherein the alignment nub cooperates with the alignment recess to removably mate thereto; and at least one indicator light that is electrically connected to the thermostat when the alignment recess and the alignment nub are mated.

2. The system of claim 1, wherein the at least one indicator light is activated when the said heat reaches and exceeds a predetermined temperature.

3. The system of claim 2, wherein the predetermined temperature is between about 96 degrees and about 99 degrees Fahrenheit.

4. The system of claim 2, wherein the power source is electronically disconnected when the alignment nub is not mated to the alignment recess.

5. The system of claim 1, wherein the spout further comprises a nozzle defining an opening communicating to the spout.

6. A method of controllably heating nasal rinsing solution inside a neti pot, comprising the steps of:
   providing a neti pot comprising: a main body forming a cavity for receiving a rinsing solution; a spout extending from a top portion of the main body; an opening defined by a top portion of the main body, wherein the opening communicates with the cavity; and a lower portion of the main body forming an alignment recess, wherein the alignment recess provides a thermostat;
   providing a heating unit comprising: a heating element electrically connected to a power source, wherein the heating element provides an outward surface for generating heat; an alignment nub formed by the outward surface, wherein the alignment nub cooperates with the alignment recess to removably mate thereto; and at least one indicator light that is electrically connected to the thermostat so that the at least one indicator light is activated when the said heat reaches a predetermined temperature;

mating the alignment recess and the alignment nub;

pouring the rinsing solution through the opening; and waiting for the at least one indicator light to by activated.

7. The method of claim 6, wherein the predetermined temperature is between about 96 degrees and about 99 degrees Fahrenheit.

8. The method of claim 6, wherein the power source is electronically disconnected when the alignment nub is not mated to the alignment recess.

9. The method of claim 6, wherein the spout further comprises a nozzle defining an opening communicating to the spout.

* * * * *